(12) United States Patent
Balke et al.

(10) Patent No.: US 11,547,879 B2
(45) Date of Patent: Jan. 10, 2023

(54) GAS MASK

(71) Applicant: Dräger Safety AG & Co. KGaA, Lübeck (DE)

(72) Inventors: Olaf Balke, Reinfeld (DE); Jan Musow, Nauen (DE); Benedikt Spiegel, Lübeck (DE)

(73) Assignee: Dräger Safety AG & Co. KGaA, Lübeck (DE)

( * ) Notice: Subject to any disclaimer, the term of this patent is extended or adjusted under 35 U.S.C. 154(b) by 447 days.

(21) Appl. No.: 16/745,536

(22) Filed: Jan. 17, 2020

(65) Prior Publication Data

US 2020/0230443 A1 Jul. 23, 2020

(30) Foreign Application Priority Data

Jan. 21, 2019 (DE) .......................... 102019000351.9

(51) Int. Cl.
*A62B 18/02* (2006.01)
*A62B 18/08* (2006.01)
*A62B 9/04* (2006.01)

(52) U.S. Cl.
CPC ................ *A62B 18/02* (2013.01); *A62B 9/04* (2013.01); *A62B 18/082* (2013.01); *A61M 2202/0208* (2013.01)

(58) Field of Classification Search
CPC .... A62B 7/00; A62B 7/02; A62B 7/10; A62B 7/12; A62B 9/00; A62B 9/04; A62B 18/00; A62B 18/006; A62B 18/02; A62B 18/025; A62B 18/04; A62B 18/08; A62B 18/082; A62B 18/10; A62B 19/00; A62B 23/00; A62B 23/02

USPC ......... 138/109; 285/114, 115, 116, 225, 229; 403/16
See application file for complete search history.

(56) References Cited

U.S. PATENT DOCUMENTS

| 4,402,316 | A | * | 9/1983 | Gadberry | ............... | A62B 18/02 |
| | | | | | | 128/201.15 |
| 4,934,361 | A | * | 6/1990 | Michel | ................... | A62B 23/02 |
| | | | | | | 128/206.17 |
| 2003/0047183 | A1 | * | 3/2003 | Kiefer | .................. | A62B 18/082 |
| | | | | | | 128/201.15 |
| 2003/0217752 | A1 | * | 11/2003 | Muller | ................... | A62B 23/02 |
| | | | | | | 128/205.27 |

(Continued)

FOREIGN PATENT DOCUMENTS

DE 701632 C 1/1941
DE 707979 C 7/1941

*Primary Examiner* — Colin W Stuart
(74) *Attorney, Agent, or Firm* — McGlew and Tuttle, P.C.

(57) ABSTRACT

A gas mask, for use with a gas filter or with a demand oxygen system, includes an elastic mask body, a connector and a counter-support. The elastic mask body is configured to be placed over the mouth and the nose of a user of the gas mask. The connector is attached to the elastic mask body and is configured to fix a gas filter or an end piece of a tube in a mount of the connector. The counter-support is attached to the elastic mask body and has a contact area for a support projection of the connector. The connector and the counter-support are arranged such that a force exerted on the connector in a direction of the user acts on the contact area of the counter-support at least partially via the support projection. The support projection is integrated at the connector by manufacturing in one piece.

20 Claims, 4 Drawing Sheets

(56) References Cited

U.S. PATENT DOCUMENTS

| | | | |
|---|---|---|---|
| 2012/0222674 A1* | 9/2012 | Ono | A62B 9/006 128/202.22 |
| 2014/0034049 A1* | 2/2014 | Castiglione | A62B 7/10 128/202.27 |
| 2015/0217144 A1* | 8/2015 | Skov | A62B 18/10 128/202.27 |

* cited by examiner

GAS MASK

CROSS REFERENCE TO RELATED APPLICATIONS

This application claims the benefit of priority under 35 U.S.C. § 119 of German Application 10 2019 000 351.9, filed Jan. 21, 2019, the entire contents of which are incorporated herein by reference.

TECHNICAL FIELD

The present invention pertains to a gas mask for use with a gas filter or with a demand oxygen system, and to a respirator system, which comprises a gas mask.

TECHNICAL BACKGROUND

Breathing protection plays a key role in the field of chemical industry and emergency management. Wherever human beings act within a toxic environment or within an environment with unknown toxicity, gas masks are used to ensure breathing protection. Gas masks are exposed to very high physical stresses especially during use by firefighters.

Gas masks that have an elastic mask body and a connector are known. The connector typically offers a possibility of connection for a gas filter and/or a demand oxygen system. For protection against contamination and flames, it is furthermore known that the connector is provided with a cap, which can be clamped onto the connector. This cap can also protect a breathing air outlet from contamination in addition to ensuring the entry of oxygen.

In view of the high physical stresses occurring during use, the architecture of a gas mask must ensure that shocks on the connector, i.e., especially also shocks on the gas filter or demand oxygen system, will not be directly transmitted to the jaw or the teeth of a user of the gas mask via the elastic mask body. It is known in this connection that such a protection against shocks can be ensured by the use of an especially rigid material when manufacturing the clampable cap. It is furthermore known that a support plate, which comes into contact with the frame of an eye-protecting lens of the gas mask in case of a shock against the connector, can be attached to the connector of a gas mask.

SUMMARY

An object of the present invention is to provide an improved gas mask, especially a gas mask with improved shock absorption against shocks acting on the connector.

To accomplish this object, a gas mask, intended for use with a gas filter or with a demand oxygen system, which gas mask has an elastic mask body, a connector and a counter-support, is proposed according to the present invention. The elastic mask body is configured to be placed over the mouth and nose of a user of the gas mask. The connector, which is attached to the elastic mask body, is configured to fix a gas filter or an end piece of a tube in a mount of the connector. The counter-support is attached to the elastic mask body and has a contact area for a support projection of the connector. The connector and the counter-support are arranged here such that a force exerted on the connector in the direction of the user of the gas mask acts on the contact area of the counter-support at least partially via the support projection, and the support projection is integrated at the connector by being manufactured in one piece with same.

The present invention is based on the discovery that shock absorption can be achieved especially efficiently and cost-effectively by integrating a support projection at the connector and by providing a corresponding counter-support at the elastic mask body.

The solution according to the present invention advantageously makes possible the use of a not especially rigid cap, i.e., of a cap that assumes a purely protective function for protection against contamination and flames.

Furthermore, the gas mask according to the present invention makes it advantageously possible to manufacture the connector and the support projection in one piece. The manufacture and attaching of an additional component, e.g., of a support plate, is avoided hereby. In addition, the use of especially rigid materials for manufacturing a cap to be attached to the connector is avoided. It is even possible to do away with the cap in the presence of a protective function integrated in the connector for protection against contamination and flames. The solution according to the present invention thus makes it possible to manufacture the gas mask in an especially cost-effective manner.

Due to the fact that the counter-support and the support projection are arranged on two different parts of the gas mask, the gas mask according to the present invention advantageously makes possible a greater mobility of the connector relative to the counter-support compared to the case of a one-piece manufacture, for example, in case of an integration of the connector in a frame of an eye-protecting lens of the gas mask. This may lead to increased resistance to fracture of the gas mask, for example, in case of tensile and transverse forces acting on the connector.

Fixation of a gas filter or of an end piece of a tube at the mount of the connector is defined within the framework of the present invention as a fixation in the direction of use of the gas filter or of the end piece in the mount. In particular, rotation of the tube, i.e., also that of a corresponding demand oxygen system connected to the tube, in the mount will be possible despite the fixation. A tube is defined here especially as the tube of a demand oxygen system, i.e., as the fixation of a demand oxygen system at the connector. A fixation is preferably brought about by screwing in via a screw thread or by a latching mechanism.

The contact area for the support projection of the connector may be larger than an actually usable contact area between the counter-support and the support projection. In particular, a variable area within the contact area can form a contact surface between the counter-support and the support projection due to a relative motion between the counter-support and the connector under the action of transverse forces acting on the gas mask.

Preferred embodiments of the gas mask according to the present invention will be described below.

In an especially advantageous embodiment of the gas mask according to the present invention, the support projection has a support surface for contacting the contact area of the counter-support and a support rib arranged at the support surface. As a result, a stable support projection is provided in an especially simple manner. To ensure a high stability of the support projection, the support rib has a width of preferably at least 0.2 cm. Furthermore, it is advantageous if the support surface and the support rib are arranged at right angles to one another. The support surface may be, for example, rectangular, triangular or semicircular. The thickness of the support surface may be lower than the width of the support rib, and it may especially be less than 0.2 cm.

In one embodiment according to the present invention, the contact area of the counter-support is configured as a contact surface. The contact area of the counter-support preferably has a flat configuration, and this contact area may especially be configured as a flat contact surface, which is arranged such that the contact area allows a flat contact of the support surface with the counter-support, i.e., a contact utilizing the entire contact surface. As a result, a force arising from a pressure or a shock on the connector is distributed especially advantageously over an area of the counter-support and of the support projection. Point loads are avoided hereby.

In an especially preferred embodiment of the gas mask, the contact area of the counter-support is larger than the support surface of the support projection. As a result, contact of the support projection with the counter-support can be ensured hereby even in the presence of transverse forces in case of a force exerted additionally in the direction of the user of the gas mask.

In a preferred embodiment of the present invention, the support projection is directed at the connector towards the nose of the user of the gas mask. This makes it possible to avoid a load acting as a point load on the lower jaw of a user of the gas mask. Such an arrangement of the support projection makes it further possible to advantageously arrange the counter-support in the area of a frame of an eye-protecting lens of the gas mask.

In one embodiment of the present invention, the support projection is configured to be in contact with the contact area of the counter-support over a width between 0.2 cm and 3 cm, preferably between 0.2 cm and 1 cm, and especially preferably between 0.2 cm and 0.5 cm. This makes possible an especially advantageous distribution of the force exerted on the connector in the direction of the user of the gas mask. A markedly smaller width would lead to an undesired point load on the counter-support.

In another embodiment of the present invention, the support projection is formed by a support surface, which extends over more than 3 cm and is integrated in the connector by a plurality of support ribs or by a contiguous support area. The contact area of the counter-support is preferably dimensioned corresponding to the support surface. An acting force can be distributed hereby over an especially large contact surface between the support surface and the contact area. In one embodiment of the present invention, which is an alternative to this, the connector has a plurality of support projections. Within the framework of this alternative embodiment, the counter-support preferably has a corresponding plurality of contact areas, and the plurality of support projections and the plurality of contact areas are arranged such that a force exerted in the direction of the user of the gas mask acts on the plurality of contact areas of the counter-support at least partially via the plurality of support projections. A corresponding force may advantageously act in this case on different contact areas of the counter-support for different directions of the force action.

In an especially preferred embodiment, the elastic mask body has a lower modulus of elasticity than the contact area of the counter-support. The elastic mask body of a gas mask is typically highly elastic in order to be able to be snugly adapted to different head shapes of the users of the gas mask. As a result, a complicated adaptation of a gas mask to a concrete user can be avoided. The more rigid contact area of the counter-support makes it possible in this embodiment to dissipate the force exerted on the connector more efficiently via the counter-support, without a local deformation (bent/deflected portion) of the elastic mask body being forced hereby.

In one embodiment according to the present invention of the gas mask, the contact area of the counter-support has approximately the same modulus of elasticity as the connector with the support projection. As a result, wear of one side of the support projection or counter-support can be avoided. Furthermore, the manufacturing costs can be reduced by reducing the amount of materials used to manufacture the gas mask.

In an especially preferred embodiment of the present invention, the counter-support is arranged at a frame of an eye-protecting lens of the gas mask. The necessity to arrange the counter-support as a separate element on the elastic mask body is avoided in this embodiment. The force exerted on the connector in the direction of the user of the gas mask can be advantageously dissipated in this embodiment via the entire frame of the eye-protecting lens and consequently over a large area via the elastic mask body to the head of the user of the gas mask. The dissipation of forces acting on the head over a large area leads to an improvement of the comfort of the user of the gas mask compared to point loads. In an especially advantageous variant of this embodiment, the counter-support is integrated at the frame by manufacture in one piece. The counter-support can be manufactured in an especially cost-effective manner in this variant of the embodiment, because no separate element needs to be manufactured. The integration in the sense of manufacturing in one piece does not mean within the framework of this variant manufacturing in one piece of the entire frame of the eye-protecting lens. Thus, the frame according to this variant of the embodiment preferably has a two-piece configuration. The counter-support is preferably arranged at the frame of the eye-protecting lens in this variant of the embodiment such that a force of the support projection, acting via the contact area in the direction of the eye-protecting lens, is at least partially absorbed by the frame. An especially stable force transmission, which is comfortable for the user of the gas mask, is made possible hereby from the connector to the entire elastic mask body.

In one preferred embodiment, the counter-support is arranged in a non-positive-locking manner at the elastic mask body. In a variant of this embodiment, the counter-support is arranged at the frame of the eye-protecting lens of the gas mask, especially integrated in the frame. The entire frame with the counter-support is arranged here in a non-positive-locking manner at the elastic mask body. The frame preferably has a two-piece configuration here and is clamped onto the elastic mask body by two screw connections. In a preferred example of this variant, the elastic mask body itself has a deformation, which makes possible a combination of non-positive locking and positive locking when the frame is arranged at the elastic mask body. As a result, the frame and the elastic mask body can be arranged especially close to one another. This is especially advantageous in view to the breathing protection function of a gas mask.

In one embodiment of the gas mask according to the present invention, the connector is attached to the elastic mask body via a connection unit. The connection unit is preferably a clamping collar. A complicated one-piece manufacturing process is avoided for the gas mask according to this embodiment by a separate manufacture of the connector and the elastic mask body. The use of a clamping collar as a connection unit makes possible an especially simple and cost-effective manufacture of the gas mask.

The gas mask according to the present invention may further have a cap on the connector for protection against contamination and flames. Contrary to prior-art caps for gas masks, the cap for the gas mask according to the present invention may be formed from a soft or at least not especially rigid material, because the cap has a purely protective function for protection against contamination and flames. Additional functional elements, which cannot be implemented within the framework of prior-art, especially rigid caps, may also be provided at the cap.

In another embodiment of the present invention, the gas mask advantageously has, in addition to the elastic mask body, a second, inner mask body for tightly enclosing the mouth and the nose. This advantageously reduces the breathing volume of the gas mask.

According to another aspect of the present invention, the object according to the present invention is accomplished by a respirator system, comprising a gas mask in accordance with at least one of the above embodiments of the present invention and a gas filter or demand oxygen system attached to the connector of the gas mask.

The respirator system according to the additional aspect of the present invention advantageously comprises the gas mask according to the present invention, as a result of which the respirator system has all the advantages of this gas mask.

The present invention will be explained now in more detail on the basis of advantageous exemplary embodiments shown schematically in the figures.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF PREFERRED EMBODIMENTS

Figure 1:
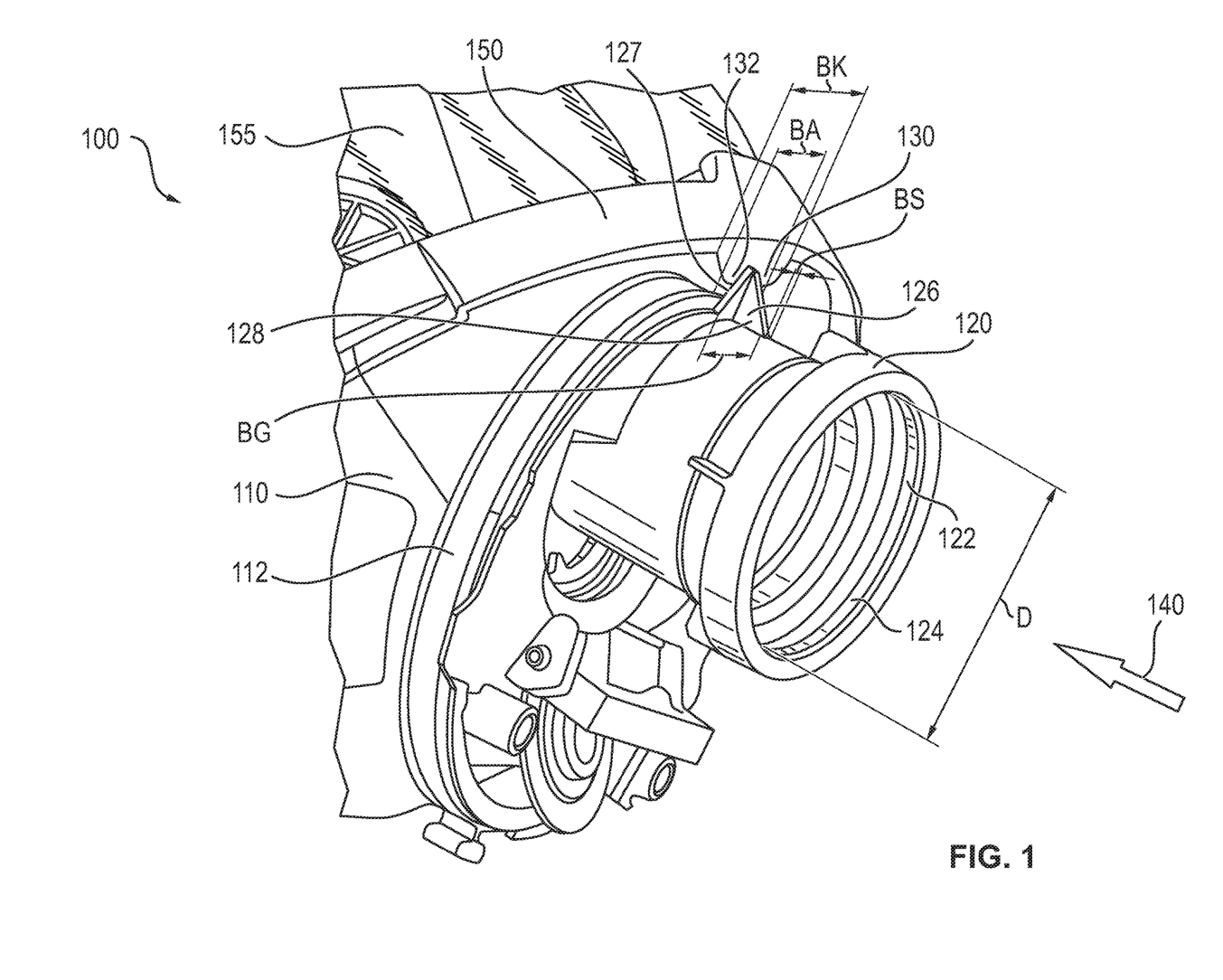
FIG. 1 is a perspective external view of a first exemplary embodiment of the gas mask according to the present invention.

Referring to the drawings, FIG. 1 shows a perspective external view of a first exemplary embodiment of the gas mask 100 according to the present invention.

The gas mask 100 has a connector 120, which is attached to an elastic mask body 110 via a connection unit 112, configured here as a clamping collar. The elastic mask body 110 is configured to be placed over the mouth and the nose of a user of the gas mask 100. The elastic mask body 110 is made of an ethylene-propylene-diene rubber (EPDM). In an alternative exemplary embodiment, the elastic mask body is made, for example, of silicone.

The connector 120 is configured to fix a gas filter or an end piece of a tube (not shown here) in a mount 122 of the connector 120. In the exemplary embodiments shown, the mount 122 has a latching mechanism 124 for latching the gas filter or the end piece of a tube. In one exemplary embodiment, not shown, the mount has a screw thread for screwing in the gas filter or the end piece of a tube. The mount 122 has an internal diameter D between 2 cm and 6 cm and preferably between 4 cm and 4.5 cm in the exemplary embodiments shown.

Furthermore, the gas mask 100 has a counter-support 130, which is attached to the elastic mask body 110 and has a contact area 132 for a support projection 126 of the connector 120. The connector 120 and the counter-support 130 are arranged here relative to one another such that a force 140 exerted on the connector 120 in the direction of the user of the gas mask 100 acts on the contact area 132 of the counter-support 130 at least partially via the support projection 126.

The support projection 126 has a support surface 127 for coming into contact with the contact area 132 of the counter-support 130 and a support rib 128 arranged at the support surface 127. The support surface 127 has a triangular configuration here, one tip of the support surface 127 having a width BS of the support rib 128 and a base of the support surface 127 having a greater width BG in the direction of the mount. The width BS of the support rib 128 is between 0.2 cm and 0.6 cm, especially between 0.2 cm and 0.3 cm, namely, about 0.25 cm in this case. The width BG of the base of the support surface 127 (only half of it can be seen in FIG. 1) is between 0.6 cm and 1.5 cm, especially preferably between 0.8 cm and 1.2 cm, and about 1 cm in this case. The support projection 126 is integrated at the connector 120 by manufacturing in one piece. The connector 120 with the support projection 126 is made of a polyamide (PA) material in this exemplary embodiments shown.

The support projection 126 is arranged in the exemplary embodiments shown at the connector 120 such that it is directed towards the nose of the user of the gas mask 100. It is advantageously made possible hereby that the counter-support 130 is arranged in the frame 150 of an eye-protecting lens 155 of the gas mask 100.

The counter-support 130 is integrated at the frame 150 by manufacturing in one piece. The frame 150 with the counter-support 130 is made of a PA material in this case. The contact area 132 of the counter-support 130 consequently has the same modulus of elasticity as the connector 120 with the support projection 126. The elastic mask body 110 has a lower modulus of elasticity than the contact area 132 of the counter-support 130. In this case, the contact area 132 is trapezoidal or approximately rectangular with a width BK between 0.2 cm and 2 cm, especially preferably between 0.2 cm and 1 cm. The contact area 132 is configured as a flat contact surface in this case. The support projection 126 is configured, furthermore, to be in contact with the contact area 132 of the counter-support 130 over a width BA between 0.2 cm and 3 cm and especially between 0.2 cm and 1 cm.

Due to the integration of the counter-support 130 in the frame 150 of the eye-protecting lens 155 of the gas mask 100, the counter-support 130 is arranged in the frame 150 such that a force of the support projection 126, acting via the contact area 132 in the direction of the eye-protecting lens 155, is at least partially absorbed by the frame 150. The frame 150 has a two-piece configuration in this case (not shown here), wherein a lower part of the frame 150 has the counter-support 130, and it is clamped with an upper part of the frame 150 to the elastic mask body 110 via two screw connections. The clamping frame formed hereby with the counter-support 130 is arranged in a predominantly non-positive-locking manner at the elastic mask body 110. The elastic mask body 110 has such a deformation (shown in FIG. 2) that the counter-support 130 is also arranged to a certain degree in a positive-locking manner at the elastic mask body 110.

Figure 2:
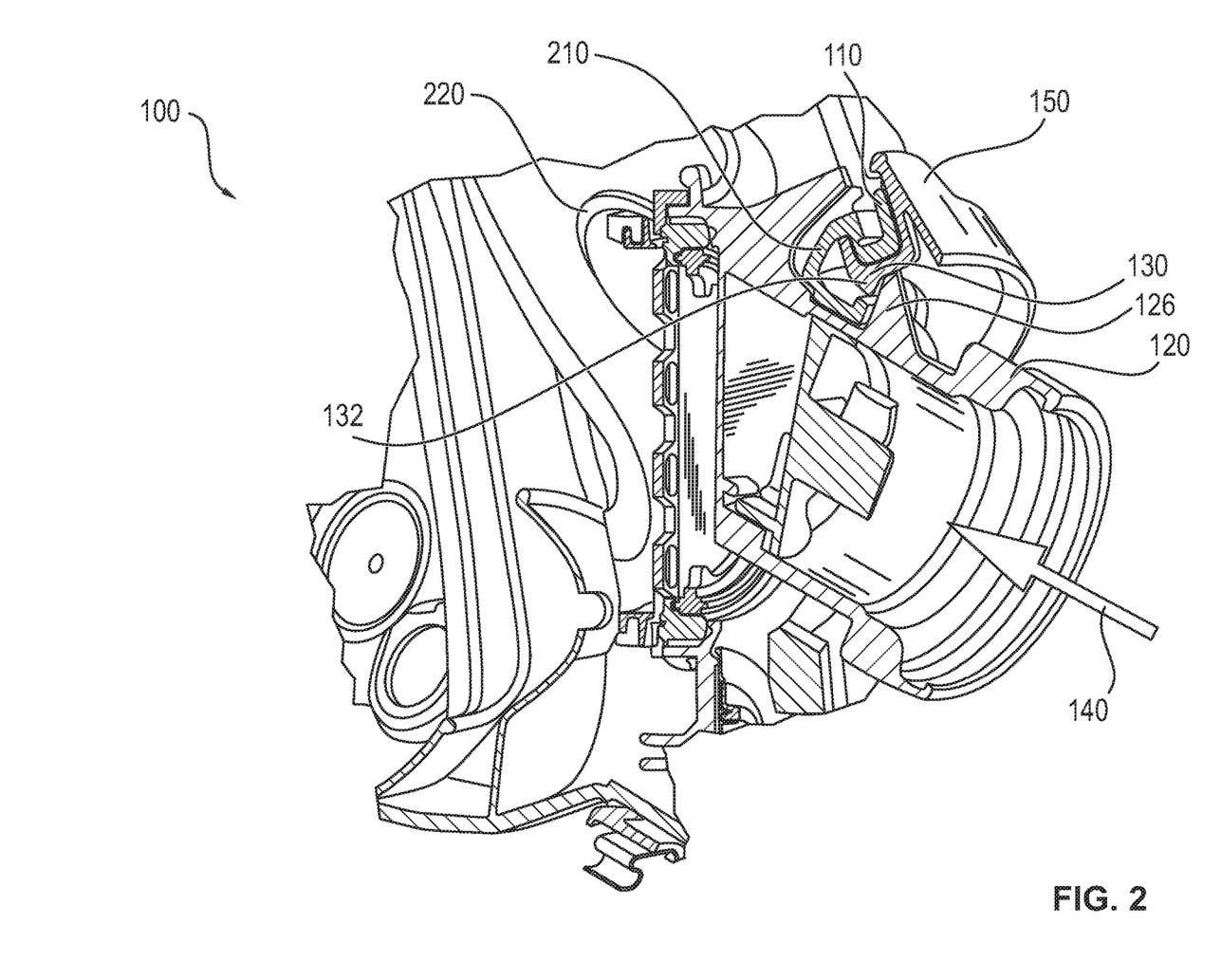
FIG. 2 is a cross sectional view of the first exemplary embodiment of the gas mask according to the present invention.

FIG. 2 shows a cross section of the first exemplary embodiment of the gas mask 100 according to the present invention.

The cross section shown illustrates the case of a force 140, which is exerted on the connector 120 in the direction of the user of the gas mask 100, by which the support projection 126 is in contact with the contact area 132 of the counter-support 130, and which acts with a corresponding proportional force component.

The elastic mask body 110 has a deformation (bent portion) 210, as a result of which the clamped frame 150 is also arranged at the elastic mask body 110 in a positive-locking manner (with positive locking engagement) in addition to a non-positive-locking fixation. As a result, the frame 150, the elastic mask body 110 and the connector 120 can be arranged especially close to one another. This is especially advantageous in view to the breathing protection function of a gas mask.

The gas mask 100 according to the first exemplary embodiment has, in addition to the elastic mask body 110, a second, inner mask body 220 for tightly enclosing the mouth and the nose. This second mask body 220 advantageously reduces a breathing volume of the gas mask 100.

Figure 3:
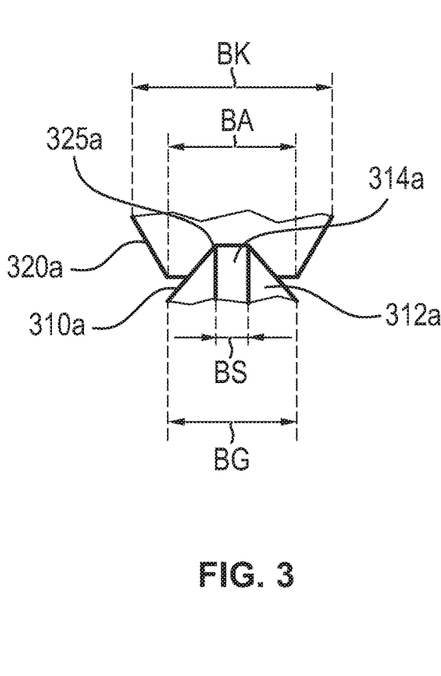
FIG. 3 is a schematic view showing one of different exemplary embodiments for a combination of support projection and counter-support, wherein the support projection is formed by a support rib and by a triangular support surface arranged at the support rib.
Figure 4:
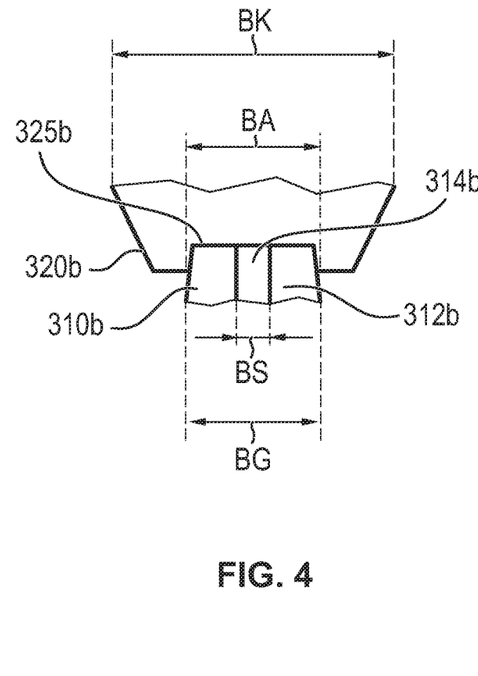
FIG. 4 is a schematic view showing one of different exemplary embodiments for a combination of support projection and counter-support, wherein the support projection is formed by a support rib and by a rectangular support surface.
Figure 5:
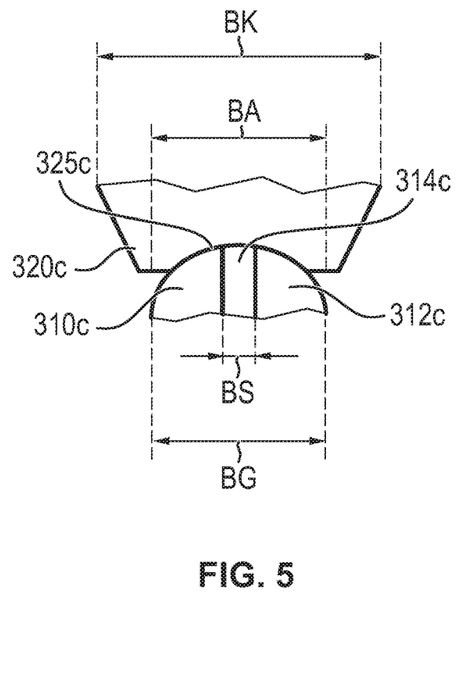
FIG. 5 is a schematic view showing one of different exemplary embodiments for a combination of support projection and counter-support, wherein the support projection is formed by a support rib and by a semicircular support surface.

FIGS. 3, 4 and 5 show three different exemplary embodiments for a combination of support projection and counter-support, wherein the support projection is formed by a support rib and a triangular support surface arranged at the support rib (FIG. 3), a rectangular support surface (FIG. 4) as well as a semicircular support surface (FIG. 5).

FIG. 3 shows a combination of a support projection 310a and counter-support 320a for an especially preferred second exemplary embodiment of the gas mask according to the present invention. The support projection 310a is formed in this case by a triangular support surface 312a and a support rib 314a arranged at right angles to the support surface 312a. The support rib 314a has a width BS of at least 0.2 cm, here about 0.25 cm. The width BG of a base of the support surface 312a is between 0.6 cm and 1.5 cm, especially between 0.8 cm and 1.2 cm, and especially about 1 cm in this case. The counter-support 320a is trapezoidal and has an approximately rectangular configuration and has a width BK between 0.6 cm and 1.7 cm and especially between 0.8 cm and 1.5 cm. A corresponding contact area 325a of the counter-support 320a is formed by a possible contact surface of the support projection 310a on the counter-support 320a. The support projection 310a is further configured to be in contact over a width BA between 0.2 cm and 1.5 cm and especially between 0.2 cm and 1 cm with the contact area 325a of the counter-support 320a.

FIG. 4 shows a combination of a support projection 310b and a counter-support 320b for a third exemplary embodiment of the gas mask according to the present invention. The support projection 310b is formed here by a trapezoidal and approximately rectangular support surface 312b and a support rib 314b arranged at right angles to the support surface 312b. The support rib 314b has a width BS of at least 0.2 cm, here about 0.25 cm. The width BG of a base of the support surface 312b is between 0.6 cm and 2 cm, especially between 0.8 cm and 1.5 cm, and about 1.2 cm in this case. The counter-support 320b is trapezoidal and has an approximately rectangular configuration and has a width BK between 0.6 cm and 2.5 cm, especially between 0.8 cm and 2 cm. A corresponding contact area 325b of the counter-support 320b is formed by a possible contact surface of the support projection 310b on the counter-support 320b. The support projection 310b is further configured to be in contact with the contact area 325b of the counter-support 320b over a width BA between 0.6 cm and 1.8 cm and especially between 0.6 cm and 1.2 cm.

FIG. 5 shows a combination of a support projection 310c and a counter-support 320c for a fourth exemplary embodiment of the gas mask according to the present invention. The support projection 310c is formed here by a semicircular support surface 312c and a support rib 314c arranged at right angles to the support surface 312c. The support rib 314c has a width BG of at least 0.2 cm, here about 0.25 cm. The width BG of a base of the support surface 312c is between 0.6 cm and 2 cm, especially between 0.8 cm and 1.5 cm, and about 1.2 cm in this case. The counter-support 320c is trapezoidal and has an approximately rectangular configuration and has a width BK between 0.6 cm and 2.5 cm and especially between 0.8 cm and 2 cm. A corresponding contact area 325c of the counter-support 320c is formed by a possible contact surface of the support projection 310c on the counter-support 320c. The support projection 310c is further configured to be in contact with the contact area 325c of the counter-support 320c over a width BA between 0.4 cm and 1.5 cm and especially between 0.4 cm and 1 cm.

Figure 6:
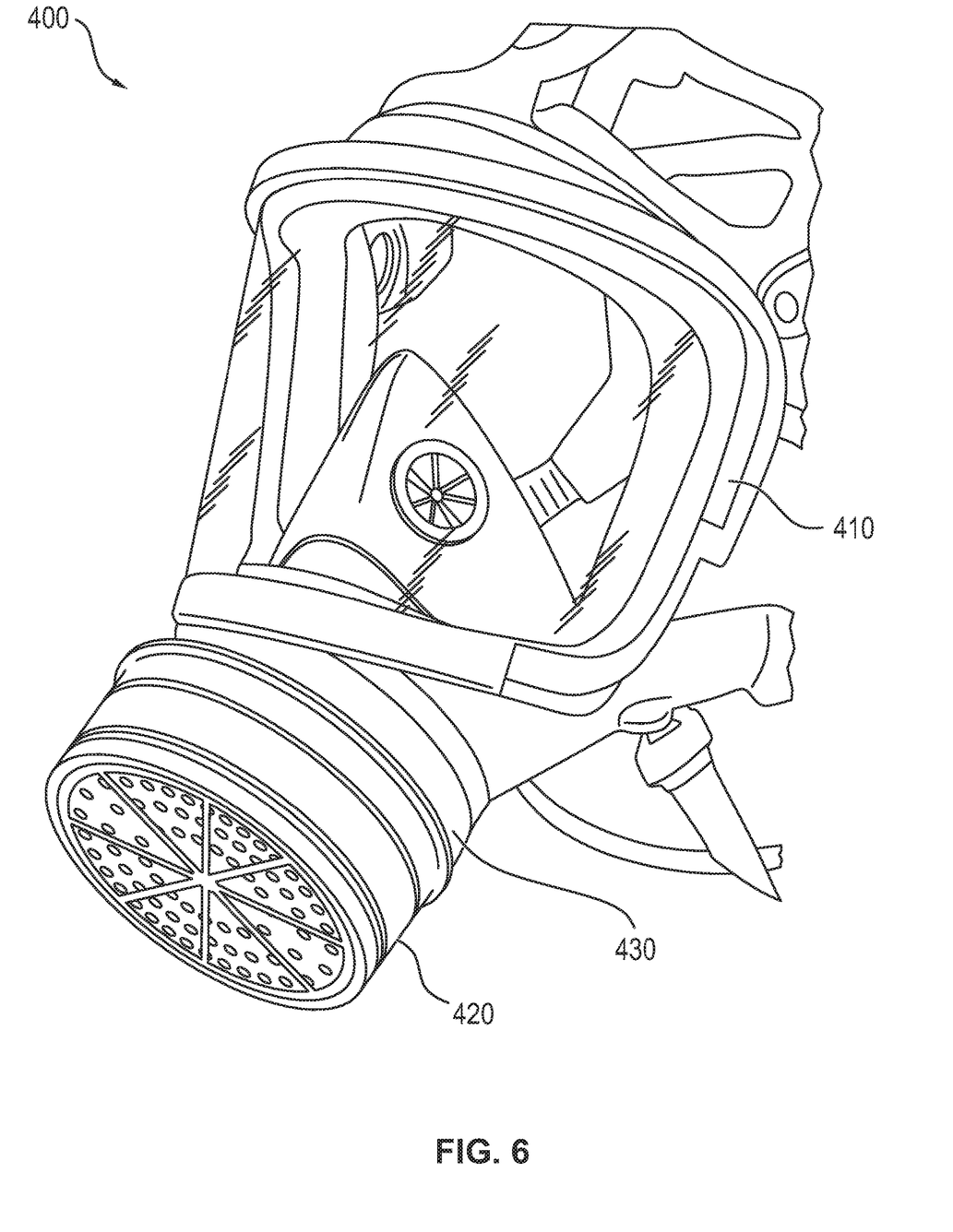
FIG. 6 is a perspective external view of an exemplary embodiment of the gas mask according to the present invention.

FIG. 6 shows a perspective external view of an exemplary embodiment of the respirator system 400 according to the present invention.

The respirator system 400 comprises a fifth exemplary embodiment of the gas mask 410 according to the present invention. The respirator system 400 further comprises a gas filter 420 attached to the connector of the gas mask 410.

In one exemplary embodiment, not shown, the respirator system comprises, instead of a gas filter, a demand oxygen system attached to the connector of the gas mask.

Furthermore, the respirator system 400 has a cap 430, which is arranged on the connector, in order to protect the connector from contamination and flames. The cap 430 is arranged at the connector by means of a latching mechanism.

While specific embodiments of the invention have been shown and described in detail to illustrate the application of the principles of the invention, it will be understood that the invention may be embodied otherwise without departing from such principles.

LIST OF REFERENCE CHARACTERS 100, 410 Gas mask
110 Elastic mask body
112 Connection unit
120 Connector
122 Mount
124 Latching mechanism
126, 310a-c Support projection
127, 312a-c Support surface
128, 314a-c Support rib
130, 320a-c Counter-support 132, 325*a-c* Contact area
140 Force exerted in the direction of the user
150 Frame
155 Eye-protecting lens
210 Deformation
220 Inner mask body
400 Respirator system
420 Gas filter
430 Cap
D Internal diameter of the mount
BA Width of the contact of the support projection at the contact area
BG Width of the base of the support surface
BK Width of the contact surface
BS Width of the support rib

What is claimed is:

1. A gas mask for use with a gas filter or with a demand oxygen system, the gas mask comprising:
an elastic mask body configured to be placed over a mouth and a nose of a user of the gas mask;
a connector attached to the elastic mask body, the connector having a support projection and being configured to fix a gas filter or fix an end piece of a tube in a mount of the connector; and
a counter-support attached to the elastic mask body, the counter-support having a contact area for contacting the support projection of the connector, wherein the connector and the counter-support are arranged such that a force exerted onto the connector in a direction of the user of the gas mask acts on the contact area of the counter-support at least partially via the support projection and wherein the support projection is integrated at the connector by manufacturing in one piece, the counter-support being arranged at a frame of an eye-protecting lens of the gas mask.

2. The gas mask in accordance with claim 1, wherein the support projection comprises:
a support surface for contacting with the contact area of the counter-support; and
a support rib arranged at the support surface.

3. The gas mask in accordance with claim 2, wherein the contact area of the counter-support has a flat configuration and is arranged such that the contact area of the counter-support allows a flat contact of the support surface with the counter-support.

4. The gas mask in accordance with claim 1, wherein the support projection at the connector is configured to be directed towards the nose of the user of the gas mask.

5. The gas mask in accordance with claim 1, wherein the support projection is configured to be in contact with the contact area of the counter-support over a width of between 0.2 cm and 3 cm.

6. The gas mask in accordance with claim 1, wherein the elastic mask body has a lower modulus of elasticity than a modulus of elasticity of the contact area of the counter-support.

7. The gas mask in accordance with claim 1, wherein the contact area of the counter-support has a same modulus of elasticity as the connector with the support projection.

8. The gas mask in accordance with claim 1, wherein the counter-support is integrated at the frame by manufacturing in one piece.

9. The gas mask in accordance with claim 1, wherein the counter-support is arranged at the frame of the eye-protecting lens such that a force of the support projection, which force acts via the contact area in a direction of the eye-protecting lens, is at least partially absorbed by the frame.

10. The gas mask in accordance with claim 1, wherein the counter-support is arranged with a non-positive-locking connection at the elastic mask body.

11. The gas mask in accordance with claim 1, further comprising a connection unit, wherein the connector is attached to the elastic mask body via the connection unit.

12. The gas mask in accordance with claim 1, wherein at least a portion of the connector is configured to extend in a direction away from the frame and the mouth of the user and the nose of the user such that the portion of the connector extends beyond the frame.

13. A respirator system comprising:
a gas mask comprising:
an elastic mask body configured to be placed over a mouth and a nose of a user of the gas mask;
a connector attached to the elastic mask body, the connector having a support projection and being configured to fix a gas filter or fix an end piece of a tube in a mount of the connector; and
a counter-support attached to the elastic mask body, the counter-support having a contact area for contacting the support projection of the connector, wherein the connector and the counter-support are arranged such that a force exerted onto the connector in a direction of the user of the gas mask acts on the contact area of the counter-support at least partially via the support projection and wherein the support projection is integrated at the connector by manufacturing in one piece, the counter-support being arranged at a frame of an eye-protecting lens of the gas mask such that a force of the support projection, which force acts via the contact area in a direction of the eye-protecting lens, is at least partially absorbed by the frame; and
a gas filter or a demand oxygen system attached to the connector of the gas mask.

14. The respirator system according to claim 13, wherein the support projection comprises:
a support surface for contacting with the contact area of the counter-support; and
a support rib arranged at the support surface.

15. The respirator system in accordance with claim 14, wherein the contact area of the counter-support has a flat configuration and is arranged such that the contact area of the counter-support allows a flat contact of the support surface with the counter-support.

16. The respirator system according to claim 13, wherein the support projection at the connector is configured to be directed towards the nose of the user of the gas mask.

17. The respirator system according to claim 13, wherein the support projection is configured to be in contact with the contact area of the counter-support over a width of between 0.2 cm and 3 cm.

18. The respirator system according to claim 13, wherein the elastic mask body has a lower modulus of elasticity than a modulus of elasticity of the contact area of the counter-support.

19. The respirator system according to claim 13, further comprising a connection unit, wherein the connector is attached to the elastic mask body via the connection unit.

20. A gas mask for use with a gas filter or with a demand oxygen system, the gas mask comprising:
an elastic mask body configured to be placed over a mouth and a nose of a user of the gas mask;
a connector attached to the elastic mask body, the connector having a support projection and being configured to fix a gas filter or fix an end piece of a tube in a mount of the connector; and a counter-support attached to the elastic mask body, the counter-support having a contact area for the support projection of the connector, wherein the connector and the counter-support are arranged such that a force exerted onto the connector in a direction of the user of the gas mask acts on the contact area of the counter-support at least partially via the support projection and wherein the support projection is integrated at the connector by manufacturing in one piece, the support projection comprising a support surface for contacting with the contact area of the counter-support and the support projection further comprising a support rib arranged at the support surface.

* * * * *